United States Patent
Coqueron et al.

(10) Patent No.: US 9,408,391 B2
(45) Date of Patent: Aug. 9, 2016

(54) FUNGICIDE COMPOSITION COMPRISING A TETRAZOLYLOXIME DERIVATIVE AND A THIAZOLYLPIPERIDINE DERIVATIVE

(75) Inventors: Pierre-Yves Coqueron, Lyons (FR); Pierre Cristau, Lyons (FR); Tomoki Tsuchiya, Lyons (FR); Ulrike Wachendorff-Neumann, Neuwied (DE)

(73) Assignee: BAYER INTELLECTUAL PROPERTY GMBH (DE)

( * ) Notice: Subject to any disclaimer, the term of this patent is extended or adjusted under 35 U.S.C. 154(b) by 182 days.

(21) Appl. No.: 13/877,737

(22) PCT Filed: Oct. 6, 2011

(86) PCT No.: PCT/EP2011/067424
§ 371 (c)(1),
(2), (4) Date: Apr. 4, 2013

(87) PCT Pub. No.: WO2012/045798
PCT Pub. Date: Apr. 12, 2012

(65) Prior Publication Data
US 2013/0190353 A1    Jul. 25, 2013

Related U.S. Application Data

(60) Provisional application No. 61/414,617, filed on Nov. 17, 2010.

(30) Foreign Application Priority Data

Oct. 7, 2010  (EP) ..................................... 10356026

(51) Int. Cl.
*A01N 43/80*  (2006.01)
(52) U.S. Cl.
CPC ...................................... *A01N 43/80* (2013.01)
(58) Field of Classification Search
CPC .. A01N 2300/00; A01N 43/713; A01N 47/18

USPC ......................................................... 514/326
See application file for complete search history.

(56) References Cited

U.S. PATENT DOCUMENTS

| | | | |
|---|---|---|---|
| 2005/0070439 A1 | 3/2005 | Kobori et al. | ................. 504/261 |
| 2009/0156592 A1 | 6/2009 | Pasteris et al. | ............. 514/232.8 |
| 2010/0240619 A1 | 9/2010 | Gregory et al. | ............... 514/154 |
| 2011/0052555 A1 | 3/2011 | Coqueron et al. | ....... 424/93.461 |
| 2011/0105566 A1 | 5/2011 | Beier et al. | ..................... 514/340 |
| 2011/0201613 A1 | 8/2011 | Beier et al. | ................. 514/237.2 |

FOREIGN PATENT DOCUMENTS

| | | |
|---|---|---|
| WO | WO 2008/013622 | 1/2008 |
| WO | WO 2008013925 A2 * | 1/2008 |
| WO | WO 2009/055514 | 4/2009 |
| WO | WO 2009/090181 | 7/2009 |
| WO | WO 2009/115557 | 9/2009 |
| WO | WO 2010/000841 | 1/2010 |
| WO | WO 2010/060982 | 6/2010 |
| WO | WO 2010/094728 | 8/2010 |
| WO | WO 2010094721 A1 * | 8/2010 |
| WO | WO 2010/123791 | 10/2010 |

OTHER PUBLICATIONS

International Search Report issued Dec. 1, 2011 in corresponding International Application No. PCT/EP2011/067424.

* cited by examiner

*Primary Examiner* — Janet Epps-Smith
*Assistant Examiner* — Courtney Brown
(74) *Attorney, Agent, or Firm* — Ostrolenk Faber LLP

(57) ABSTRACT

The present invention relates to a pesticide composition intended for protecting plants, crops or seeds against fungal diseases or insect damages, and the corresponding methods of protection by application of the said composition. More precisely, the subject of the present invention is a pesticide composition based on a tetrazolyloxime derivative and a thiazolylpiperidine derivative, which may further comprise another fungicide and/or an insecticide active substance or compound.

13 Claims, No Drawings

FUNGICIDE COMPOSITION COMPRISING A TETRAZOLYLOXIME DERIVATIVE AND A THIAZOLYLPIPERIDINE DERIVATIVE

CROSS REFERENCE TO RELATED APPLICATION(S)

The present application is a 35 U.S.C. §371 national phase conversion of PCT/EP2011/067424 filed on Oct. 6, 2011, which claims priority to European Application No. 10356026.4 filed on Oct. 7, 2010 and U.S. Provisional Application No. 61/414,617 filed on Nov. 17, 2010. Applicants claim priority to each of the foregoing patent applications. The PCT International Application was published in the English language.

DESCRIPTION

The present invention relates to a pesticide composition intended for protecting plants, crops or seeds against fungal diseases or insect damages, and the corresponding methods of protection by application of the said composition. More precisely, the subject of the present invention is a pesticide composition based on a tetrazolyloxime derivative and a thiazolylpiperidine derivative, which may further comprise another fungicide and/or an insecticide active substance or compound.

As regards pesticide activity, in particular for the protection of crops, one of the problems at the heart of the research studies carried out in this technical field is the improvement of performances, in particular in terms of biological activity and in particular in terms of maintaining such an activity over time.

The present invention provides a pesticide composition which can be used, in particular by the farmer, for controlling the pest infesting crops and in particular for controlling insects or diseases.

The pesticide compounds useful for the protection of plants must be endowed with an ecotoxicity which is reduced to the minimum. As far as possible, they should not be dangerous or toxic to the operator during use. The economic factor should of course not be overlooked in the search for novel pesticide agents.

The present invention advantageously provides a pesticide composition which is completely high-performing in particular as regards its efficacy against pests and the perennially of this efficacy so as to be able to reduce the doses of chemical products spread in the environment for combating pest damages or attacks of plants or crops.

The invention provides a pesticide composition capable to be more active and active for longer, and which therefore has a lower dose, but which is also less toxic, in particular in the treatment of plants and particularly the foliar and seed treatments of fungal diseases or the control of insects, for example, of cereals, cotton, peanut, bean, beet, canola, Solanaceae, grapevine, vegetables, lucerne, soybean, market garden crops, turf, wood or horticultural plants.

The composition according to the invention allows controlling a broad variety of insects or fungi. For example, the pesticide composition according to the invention exhibits an improved efficacy against fungus like *Plasmodiophoromycetes, Oomycetes, Chytridiomycetes, Zygomycetes, Basidiomycetes, Deuteromycetes* and *Ascomycetes*.

All these objectives or advantages, among others, were achieved by finding a pesticide composition comprising a tetrazolyloxime derivative and a thiazolylpiperidine derivative, which may further comprise an other fungicide and/or an insecticide active substance or compound. Such a composition surprisingly and unexpectedly allows a very high and perennial anti-fungal or insecticide efficacy against a broad spectrum of insects or fungi and in particular against those responsible for diseases or damages of crops. Other insect pests or diseases of crops can be controlled with the pesticide composition according to the invention.

The pesticide composition according to the invention may also be used for the treatment of bacterial or virus diseases.

Insects or nematodes that can be controlled with the pesticide composition according to the invention include a broad variety of these damaging organisms.

In patent application US-2005/0070439 there are disclosed certain tetrazolyloxime derivatives. The possibility to mix said compounds with other chemicals is generally mentioned. However, there is no specific disclosure in this document of any combination comprising said tetrazolyloxime derivatives with a fungicide compound.

In patent applications WO-2009/119072 and WO-2010/094728, there are disclosed certain tetrazolyloxime derivatives for which the possibility to mix said compounds with other chemicals is mentioned. However, there is no specific disclosure in this document of any combination comprising said tetrazolyloxime derivatives with a thiazolylpiperidine derivative.

In patent application WO-2008/013925 there are disclosed certain thiazolylopiperidine derivatives. The possibility to mix said compounds with other chemicals is generally mentioned. However, there is no specific disclosure in this document of any combination comprising said tetrazolyloxime derivatives with a fungicide compound.

In patent application WO-2009/055514, there are disclosed certain thiazolylpiperidine derivatives for which the possibility to mix said compounds with other chemicals is mentioned. However, there is no specific disclosure in this document of any combination comprising said thiazolylpiperidine derivatives with a tetrazolyloxime derivative.

In a main aspect, the present invention provides a composition comprising:
A) a tetrazolyloxime derivative of formula (I)

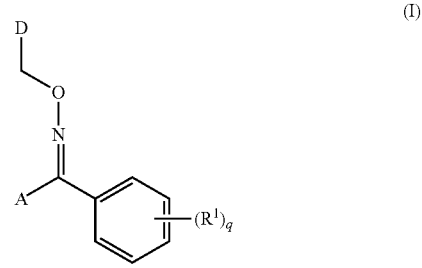

(I)

wherein
R independently represents a hydrogen atom, a halogen atom, a substituted or non-substituted $C_1$-$C_6$-alkyl, a substituted or non-substituted $C_1$-$C_6$-alkoxy, nitro, cyano, a substituted or non-substituted $C_1$-$C_6$-aryl or a substituted or non-substituted $C_1$-$C_6$-alkylsulfonyl;
q represents 0, 1, 2, 3, 4 or 5;
A represents a tetrazoyl group of formula (A) or ($A^2$):

($A^1$)

($A^2$)

wherein Y represents an $C_1$-$C_6$-alkyl group; and
D represents a pyridyl group of formula ($D^1$) or a thiazolyl group of formula ($D^2$);

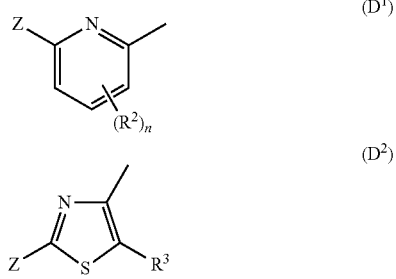

wherein $R^2$ and $R^3$ independently represent a hydrogen atom, a halogen atom, a substituted or non-substituted $C_1$-$C_8$-alkyl, nitro, cyano, a hydroxy group, a mercapto group, formyl, hydroxycarbonyl, a substituted or non-substituted amino, a substituted or non-substituted $C_2$-$C_8$-alkenyl, a substituted or non-substituted $C_2$-$C_8$-alkynyl, a substituted or non-substituted aryl, a substituted or non-substituted heterocyclyl, $OR^a$, $S(O)_rR^a$, $COR^a$ or $CO_2R^a$; wherein $R^a$ represents a substituted or non-substituted $C_1$-$C_8$-alkyl, a substituted or non-substituted amino, a substituted or non-substituted $C_3$-$C_8$-cycloalkyl, a substituted or non-substituted $C_2$-$C_8$-alkenyl, a substituted or non-substituted $C_2$-$C_8$-alkynyl, a substituted or non-substituted aryl; wherein, r represents 0, 1 or 2;
wherein n represents 0, 1, 2 or 3;
wherein Z represents $Q^1CONH$—, wherein represents a substituted or non-substituted $C_1$-$C_8$-alkyl, a substituted or non-substituted $C_1$-$C_8$-alkoxy, a substituted or non-substituted $C_2$-$C_8$-alkynyloxy;
as well as salts, N-oxides, metallic complexes and metalloidic complexes thereof or (E) and (Z) isomers and mixtures thereof
and
B) a thiazolylpiperidine derivative of formula (II)

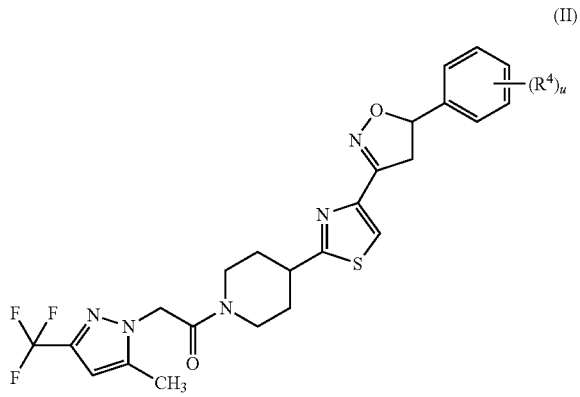

wherein
$R^4$ independently represents a hydrogen atom, a halogen atom, a $C_1$-$C_8$-alkyl, a $C_1$-$C_8$-alkoxy, a $C_1$-$C_8$-haloalkyl comprising between one and 5 halogen atoms, cyano;
u represents 1, 2, 3, 4 or 5;
as well as salts, N-oxides, metallic complexes and metalloidic complexes thereof or optically active isomers and mixtures thereof
in an A/B weight ratio ranging from 1,000/1 to 1/1,000.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

Notably, the stereostructure of the oxime moiety present in the tetrazolyloxime derivative of formula (I) includes (E) or (Z) isomer, and these stereoisomers form part of the present invention.

According to the invention, the following generic terms are generally used with the following meanings:
halogen means fluorine, chlorine, bromine or iodine
heteroatom can be nitrogen, oxygen or sulfur;
unless indicated otherwise, a group or a substituent that is substituted according to the invention can be substituted by one or more of the following groups or atoms: a halogen atom, a nitro group, a hydroxy group, a cyano group, an isocyano group, an isocyanate group, an thiocyanate group, an amino group, a sulfenyl group, a formyl group, a formyloxy group, a carbamoyl group, a $C_1$-$C_8$-alkyl, a $C_1$-$C_8$-halogenoalkyl having 1 to 5 halogen atoms, a $C_2$-$C_8$-alkenyl, a $C_2$-$C_8$-alkynyl, a $C_2$-$C_8$-alkenyloxy, a $C_1$-$C_8$-alkylamino, a di-$C_1$-$C_8$-alkylamino, a phenylamino, a benzylamino, a phenethylamino, a $C_1$-$C_8$-alkoxy, a $C_1$-$C_8$-halogenoalkoxy having 1 to 5 halogen atoms, a $C_1$-$C_8$-alkylsulfenyl, a $C_1$-$C_8$-alkylcarbonyl, a $C_1$-$C_8$-alkylthiocarbonyl, a $C_1$-$C_8$-alkylcarbamoyl, a di-$C_1$-$C_8$-alkylcarbamoyl, a $C_1$-$C_8$-alkoxycarbonyl, a $C_1$-$C_8$-alkylcarbonyloxy, a $C_1$-$C_8$-alkylcarbonylamino, $C_1$-$C_8$-alkoxycarbonylamino, a $C_1$-$C_8$-alkylsulfenyl, a $C_1$-$C_8$-alkylsulfonyl, a $C_2$-$C_8$-alkenylsulfonyl, a $C_8$-$C_8$-alkynylsulfonyl, aryl-sulfonyl, saturated or unsaturated 4-, 5-, 6- or 7-membered heterocyclylsulfonyl, aryl-[$C_1$-$C_8$]-alkylsulfonyl, a $C_1$-$C_8$-alkylsulfamoyl, a $C_1$-$C_8$-halogenoalkyl sulfamoyl having 1 to 5 halogen atoms, a N-di($C_1$-$C_8$-alkyl)sulfamoyl, a N-di($C_1$-$C_8$-halogenoalkyl)sulfamoyl having 1 to 5 halogen atoms, arylsulfamoyl, saturated or unsaturated 4-, 5-, 6- or 7-membered heterocyclylsulfamoyl aryl-[$C_1$-$C_8$]-alkyl, saturated or unsaturated 4-, 5-, 6- or 7-membered heterocyclyl-[$C_1$-$C_8$]-alkyl comprising up to 4 heteroatoms selected in the list consisting of N, O, S, aryl-[$C_1$-$C_8$]-alkoxy, aryloxy, aryl, ($C_1$-$C_8$-alkylimino)-$C_1$-$C_8$-alkyl, saturated or unsaturated 4-, 5-, 6- or 7-membered heterocyclyl, aryl-[$C_1$-$C_8$]-alkylthio, arylthio, saturated or unsaturated 4-, 5-, 6- or 7-membered heterocyclylthio;
the term "aryl" means phenyl or naphthyl
the term "heterocyclyl" means saturated or unsaturated 4-, 5-, 6- or 7-membered heterocyclyl.

In a further aspect, the present invention provides a composition comprising:
A) a tetrazolyloxime derivative of formula (I) wherein formula (I) is as herein-defined ;
B) a thiazolylpiperidine derivative of, formula (II) wherein formula (II) is, as, herein-defined and
C) a third further fungicide compound in an A/B/C weight ratio ranging from 1,000/1,000/1 to 1/1,000/1,000.

Still in a further aspect, the present invention provides a composition comprising:
A) a tetrazolyloxime derivative of formula (I) wherein formula (I) is as herein-defined;
B) a thiazolylpiperidine derivative of formula (II)) wherein formula (II) is as herein-defined and
D) an insecticide compound in an A/B/D weight ratio ranging from 1,000/1,000/1 to 1/1,000/1,000.

Still in a further aspect, the present invention provides a composition comprising:
A) a tetrazolyloxime derivative of formula (I) wherein formula (I) is as herein-defined;
B) a thiazolylpiperidine derivative of formula (II) wherein formula (II) is as herein-defined;
C) a third further fungicide compound and
D) an insecticide compound in an A/B/C/D weight ratio ranging from 1,000/1,000/1,000/1 to 1/1,000/1,000/1,000.

In the tetrazolyloxime derivative of formula (I), the substitution position of $R^1$ is not specifically limited and $R^1$ represents preferentially a hydrogen atom, a halogen atom, a substituted or non-substituted $C_4$-$C_6$-alkyl, a substituted or non-substituted $C_1$-$C_6$-alkoxy.

The alkyl group represented for $R^1$ is preferably an alkyl group having 1 to 4 carbon atoms and specific examples thereof include a methyl group, an ethyl group, a n-propyl group, an isopropyl group, a n-butyl group, an isobutyl group, a sec-butyl group, and a tert-butyl group. Among these alkyl groups, a methyl group or a tert-butyl group is particularly preferred.

The $C_1$-$C_8$-alkoxy group for $R^1$ is preferably alkoxy group having 1 to 3 carbon atoms and specific examples thereof include a methoxy group, an ethoxy group, a propoxy group, and an isopropoxy group. Among these alkoxy groups, a methoxy group or an ethoxy group is particularly preferred.

$R^1$ represents more preferentially a hydrogen atom or a halogen atom.

In the tetrazoyl group of formula ($A^1$) or ($A^2$), Y represents an alkyl group. Among these alkyl groups, an alkyl group having 1 to 3 carbon atoms such as a methyl group, an ethyl group, a n-propyl group or an isopropyl group is preferable. Among these alkyl groups, a methyl group is particularly preferred.

$R^2$ and $R^3$ independently represent preferentially a hydrogen atom or a halogen atom.

For the tetrazolyloxime derivative of formula (I), preference is further given to but-3-yn-1-yl{6-[({[(Z)-(1-methyl-1H-tetrazol-5-yl)(phenyl)methylene]amino}oxy)methyl]pyridin-2-yl}carbamate (compound A1) and to
tert-butyl{6-({[[(Z)-(1-methyl-1H-tetrazol-5-yl)(phenyl)methylene]amino}oxy)methyl]pyridin-2-yl}carbamate (compound A2)

Compound A1

Compound A2

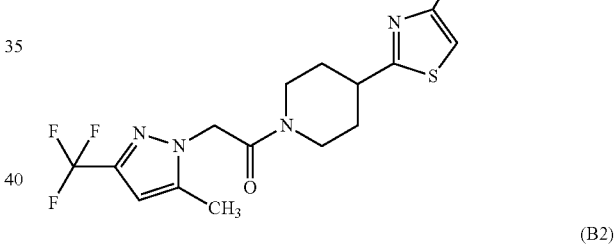

The stereostructure of the oxime moiety present in the tetrazolyloxime derivative of formula (I) includes (E) or (Z) isomer, and these stereoisomers form part of the present invention. The synthesized product is generally obtained in the form of the (Z) isomer or a mixture of (E) and (Z) isomers, each of which can be isolated by separation or purification.

In the tetrazolyloxime derivative of formula (I), the (Z) isomer is particularly superior to the (E) isomer in plant disease controlling activity. However, both the (E) isomer and the (Z) isomer generally exist in a fixed ratio in the form of a mixture since the (Z) isomer is generally converted into the (E) isomer by light in a natural environment. The stable ratios of the (E) and (Z) isomers vary according to the type of compound.

In the thiazolylpiperidine derivative of formula (II), $R^4$ represents preferentially a hydrogen atom or a halogen atom. More preferably, $R^4$ represents preferentially a hydrogen atom or a fluorine For thiazolylpiperidine derivative of formula (II), preference is further given to 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (compound B1) and to
1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (compound B2)

(B1)

(B2)

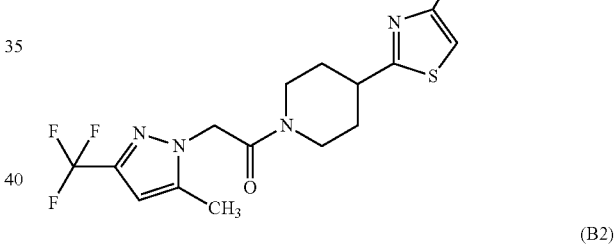

For the different aspects of the composition according to the invention, fungicide compounds C can be independently selected in the list consisting of:
(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-

68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-443-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-3), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-([4-(trifluoromethyl)pyridin-2-yl]oxy]phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for, example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]Phenyl)-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32)2424(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulfur and sulfur preparations including calcium polysulfide (7704-34-9), (5.31) thiram (137-26-8), (5.32) tolylfluanid (731-27-1), (5.33) zineb (12122-67-7) and (5.34) ziram (137-30-4).

(6) Compounds capable, to induce a host defence, for example (6.1) acibenzolar-S-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (VV02005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9),:(10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl (3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5) chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3- dimethylbutan-2-yl 1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c']dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 245-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67)3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (W02009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino] [6-(difluoromethoxy)-2,3-difluorophenyl]methyl)-2-phenylacetamide (221201-92-9), (15.85) N-{(Z)-[(cyclopropylmethoxy)imino][6-(difluoromethoxy)-2,3-difluorophenyl]methyl)-2-Phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl] acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy)methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6-[({[(1-methyl-1H-tetrazol-5-yl)(phenyl)methylene]amino}oxy)methyl]pyridin-2-yl}carbamate.

(16) Further compounds, for example (16.1) 1-methyl-3-(trifluoromethyl)-N[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N44'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-Abiphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N14'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl) prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl {6-[({[(Z)-(1-methyl-1H-tetrazol-5-yl)(phenyl)methylene]amino}oxy)methyl]pyridin-2-yl}carbamate.

All named mixing partners of the classes (1) to (16) can, if their functional groups enable this, optionally form salts with suitable bases or acids.

For the different aspects of the composition according to the invention, insecticide compound D is preferably selected in the list consisting of:

(1) Acetylcholinesterase (AChE) inhibitors, for example
carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thio-fanox, triazamate, trimethacarb, XMC, and xylylcarb; or organophosphates, e.g. acephate, azarnethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion(-methyl), phenthoate, phorate, phosalone, phosmet, phosphamidon, phoxim, pirimiphos(-methyl), profenofos, propetamphos, prothiofos, pyraclofos, pyridaphenthion, quinalphos, sulfotep, tebupirirnfos, temephos, terbufos, tetrachlorvinphos, thiometon, triazophos, triclorfon, and vamidothion.

(2) GABA-gated chloride channel antagonists, for example
organochlorines, e.g. chlordane, endosulfan (alpha-); or fiproles (phenylpyrazoles), e.g. ethiprole, fipronil, pyraflu-prole, and pyriprole.

(3) Sodium channel modulators/voltage-dependent sodium channel blockers, for example pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta:), cyhalothrin (gamma-,lambda-), cypermethrin (alpha-, beta-, theta-, zeta-), cyphenothrin [(1R)-trans-isomers], deltamethrin, dimefluthrin, empenthrin [(EZ)-(1 R)-isomers), esfenvalerate, etofenprox, fenpropathrin, fenvalerate, flucythrinate, flumethrin, fluvalinate (tau-), halfenprox, imiprothrin, nietofluthrin, permethrin, phenothrin [(1R)-trans-isomer), prallethrin, profluthrin, pyrethrin (pyrethrum), resmethrin, RU 15525, silafluofen, tefluthrin, tetramethrin [(1R)- isomers)], tralomethrin, transfluthrin and ZXI 8901; or
DDT; or methoxychlor.

(4) Nicotinergic acetylcholine receptor agonists, for example
chloronicotinyls, e.g. acetamiprid, clothianidin, dinotefuran, imidacloprid, nitenpyram, thiacloprid, thiamethoxam,; or nicotine.

(5) Allosteric acetylcholine receptor modulators (agonists), for example spinosyns, e.g. spinetoram and spinosad.

(6) Chloride channel activators, for example avermectins/milbemycins, e.g. abamectin, emamectin benzoate, lepimectin, and milbemectin.

(7) Juvenile hormone mimics, e.g. hydroprene, kinoprene, methoprene; or fenoxycarb; pyriproxyfen.

(8) Miscellaneous non-specific (multi-site) inhibitors, for example gassing agents, e.g. methyl bromide and other alkyl halides; or chloropicrin; sulfuryl fluoride; borax; tartar emetic.

(9) Selective homopteran feeding, blockers, e.g. pymetrozine; or flonicamid.

(10) Mite growth inhibitors, e.g. clofentezine, diflovidazin, hexythiazox, etoxazole.

(11) Microbial disruptors of insect midgut membranes, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example diafenthiuron; or
organotin miticides, e.g. azocyclotin, cyhexatin, and fenbutatin oxide; or
propargite; tetradifon.

(13) Uncouplers of oxidative phoshorylation via disruption of the proton gradient, for example chlorfenapyr, and DNOC.

(14) Nicotinic acetylcholine receptor channel blockers, for example bensultap, cartap hydrochloride, thiocyclam, and thiosultap-sodium.

(15) Inhibitors of chitin biosynthesis, type 0, for example benzoylureas, e.g. bistrifluron, chlorfluazuron, diflubenzuron, flucycloxuron, flufenoxuron, hexaflumuron, lufenuron, novaluron, noviflumuron, penfluron, teflubenzuron, and triflumuron.

(16) Inhibitors of chitin biosynthesis, type 1, for example buprofezin.

(17) Moulting disruptors, for example cyromazine.

(18) Ecdysone receptor agonists/disruptors, for example diacylhydrazines, e.g. chromafenozide, halofenozide, methoxyfenozide, and tebufenozide.

(19) Octopamine receptor agonists, for example amitraz.

(20) Mitochondria complex III electron transport inhibitors (Coupling site II), for example hydramethylnon; acequinocyl; fluacrypyrim; or cyflumetofen and cyenopyrafen.

(21) Mitochondrial complex I electron transport inhibitors, for example
METI acaricides, e.g. fenazaquin, fenpyroximate, pyrimidifen, pyridaben, tebufenpyrad, tolfenpyrad;
or rotenone. (Derris).

(22) Voltage-dependent sodium channel blockers, e.g. indoxacarb; metaflumizone.

(23) Inhibitors of acetyl CoA carboxylase, for example tetronic acid derivatives, e.g. spirodiclofen and spiromesifen; or
tetramic acid derivatives, e.g. spirotetramat.

(24) Mitochondrial complex IV electron inhibitors, for example phosphines, e.g. aluminium phosphide, calcium phosphide, phosphine, and zinc phosphide;
or cyanide.

(28) Ryanodine receptor modulators, for example diamides, e.g. chlorantraniliprole (Rynaxypyr), Cyantraniliprole (Cyazypyr), and flubendiamide.

Further active ingredients with unknown or uncertain mode of action, for example azadirachtin, amidoflumet, benzoximate, bifenazate, chinomethionat, cryolite, dicofol, flufenerim, pyridalyl, and pyrifluquinazon; or one of the following known active compounds 4-{[(6-brompyrid-3-yl)methyl](2-fluorethyl) amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/ 115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2 (5H)-on (known from WO 2007/115646), 4-{[(6-chlor-5-fluorpyrid-3-yl)methyl]cyclopropyl)amino}furan-2(5H)-on (known, from WO 2007/115643), 4-{[(6-chlorpyrid-3-yl) methyl](cyclopropyl)amino}furan-2(5H)-on (known from EP-A-0 539 588), 4-{[(6-chlorpyrid-3-yl)methyl](methyl) amino}furan-2(5H)-on (known from EP-A-0 539 588), [(6-chlorpyridin-3-yl)methyl](methyl)oxido-$\lambda^4$-sulfanylidencyanamid (known from WO 2007/149134), [1-(6-chlorpyridin-3-yl)ethyl](methyl)oxido-$\lambda^4$-sulfanylidencyanamid (known from WO 2007/149134) and its diastereomeres (A) and (B)

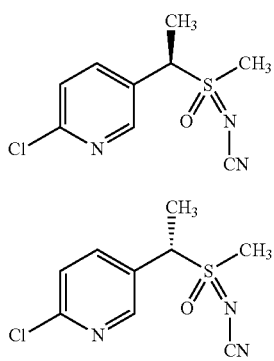

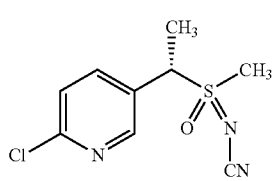

(also known from WO 2007/149134), [(6-trifluormethylpyridin-3-yl)methyl]methyl)oxido-λ⁴-sulfanylidencyanamid (known from WO 2007/095229), or sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), and 1-{2,4-dimethyl-5-[(2,2,2-trifluoroethyl)sulfinyl]phenyl}-3-(trifluoromethyl)-1H-1,2,4-triazole (known from WO 1999/55668).

The active ingredients specified in this description by their "common name" are known, for example, from "The Pesticide Manual", 14th Ed., British Crop Protection Council 2006, and from the Web page http://www.alanwood.net/pesticides.

For the various aspects of the composition according to the invention, more preferred insecticide compounds are selected in the list consisting of imidacloprid and clothianidin.

For the composition according to the invention, the NB weight ratio preferably ranges from 1/0.01 to 1/100; more preferably from 1/0.05 to 1/80.

For the composition according to the invention, the A/B/C or A/B/D weight ratio preferably ranges from 1/0.01/0.01 to 1/100/100; more preferably from 1/0.05/0.05 to 1/80/80. For the composition according to the invention, the A/B/C/D weight ratio preferably ranges from 1/0.01/0.01/0.1 to 1/100/100/100; more preferably from 1/0.05/0.05/0.5 to 1/80/80/80.

Particular compositions according to the invention are defined as combining all or part of:
preferred oxime compounds of formula (I) as herein-defined;
referred thiazolylpiperidine derivative of formula (II) as herein-defined;
preferred fungicide compounds C;
preferred insecticide compounds D;
preferred weight ratios of active substances.

According to another aspect of the present invention, in the pesticide composition according to the invention, the compound ratio A/B can be advantageously selected so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = X + Y - \frac{XY}{100}$$

wherein E represents the expected percentage of inhibition of the pest for the combination of the two compounds at defined doses (for example equal to x and y respectively), X is the percentage of inhibition observed, for the pest by compound A at a defined dose (equal to x), Y is the percentage of inhibition observed for the pest by, compound B at a defined dose (equal to y). When the percentage of inhibition observed for the combination is greater than E, there is a synergistic effect.

The term "synergistic effect" also means the effect defined by application of the Tammes method, "Isoboles, a graphic representation of synergism in pesticides", Netherlands Journal of Plant Pathology, 70(1964), pages 73-80.

According to another aspect of the present invention, in the pesticide composition according to the invention, the compound ratio A/B/C can be advantageously selected so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = X + Y + Z - \frac{XYZ}{100}$$

wherein E represents the expected percentage of inhibition of the pest for the combination of the three compounds at defined doses (for example equal to x, y and z respectively), X is the percentage of inhibition observed for the pest by compound A at a defined dose (equal to, x), Y is the percentage of inhibition observed for the pest by compound B at a defined dose (equal to y) and Z is the percentage of inhibition observed for the pest by, compound C at a defined dose (equal to z). When the percentage of inhibition observed for the combination is greater than E, there is a synergistic effect.

The term "synergistic effect" also means the effect, defined by, application of the Tammes to method, "Isoboles, a graphic representation of synergism in pesticides", Netherlands Journal of Plant Pathology, 70(1964), pages 73-80.

Synergistic compositions comprising further active substances also form part of the present invention, the associated synergistic effect can be evidenced in a similar manner.

The pesticide composition according to the invention may comprise from 0.00001 to 100%, preferably from 0.001 to 80%, of active compounds, whether these compounds are combined or whether they are in, the form of two or more active ingredients used separately.

More generally, the pesticide composition according to the invention may eventually also comprise one or more other active substances selected from fungicide, herbicide, insecticide or plant growth regulator active compounds.

In addition to these additional active agents, the pesticide composition according to the invention, may also comprise, any other adjuvants or auxiliary agent useful in plant protection formulations such as, for example, an, agriculturally suitable inert carrier and optionally, an agriculturally suitable surfactant.

For its practical use, the pesticide composition according to the invention can be used alone or in formulations containing, one or the other of the active ingredients or alternatively both of them together, in combination or association with one or, more other compatible components which are, for example, solid or liquid fillers or diluents, adjuvants, surfactants or equivalents, which are suitable for the desired use and which are acceptable for uses in agriculture. The formulations can be of any type known in the sector that is suitable for application onto all types of cultures or, crops. These, formulations, which can be prepared in any manner known by, the skilled person, also form part of the invention.

The formulations may also contain ingredients of other types, such as protective colloids, adhesives, thickeners, thixotropic agents, penetrating agents, oils for, spraying, stabilisers, preserving agents (in particular mould-proofing or biocide agents), sequestering or chelating agents or the like. More generally, the compounds used in the invention can be combined with any solid or liquid additives corresponding to the usual formulation techniques.

The term "filler" means an organic or inorganic, natural or synthetic component with which the active components are combined to facilitate its application, for example, onto the plants, the seeds or the soil. This filler is consequently generally inert and it must be acceptable (for example acceptable for agronomic uses, in particular for treating plants).

The filler can be solid, for example clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths or synthetic minerals, such as silica, alumina or silicates, in particular aluminium or magnesium silicates.

The solid fillers which are suitable for granules are as follows: natural, crushed or broken rocks, such as calcite, marble, pumice, sepiolite and dolomite; synthetic granules of inorganic or organic flours; granules of organic material such as sawdust, coconut shell, corn ear or envelope or tobacco stem; kieselguhr, tricalcium phosphate, powdered cork or adsorbent carbon black; water-soluble polymers, resins, waxes; or solid fertilizers. Such composition may, if so desired, contain one or more compatible agents such as wetting agents, dispersing agents, emulsifiers or colourings which, when they are solid, may also act as diluents.

The fillers may also be liquid, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulfoxide, N,N-dimethyl-acetamide or N-methylpyrrolidone; N-octylpyrrolidone, liquefied gases; or the like, whether they are taken separately or as a mixture.

The surfactant can be an emulsifier, a dispersing agent or a wetting agent, of ionic or nonionic type or a mixture of these surfactants. Among those surfactants there are used, for example, polyacrylic acid salts, lignosulfonic acid salts, phenolsulfonic or naphthalenesulfonic acid salts, polycondensates of ethylene oxide with fatty alcohols or fatty acids or fatty esters or fatty amines, substituted phenols (in particular alkylphenols or arylphenols), ester-salts of sulfosuccinic acid, taurine derivatives (in particular alkyl taurates), phosphoric esters of alcohols or of polycondensates of ethylene oxide with phenols, fatty acid esters with polyols or sulfate, sulfonate or phosphate functional derivatives of the compounds described above. The presence of at least one surfactant is generally essential when the active ingredients and/or the inert filler are, insoluble or only sparingly soluble in water, and when the filler for the said composition to be applied is water.

The formulations may also contain other additives such as adhesives or dyes. Adhesives such as carboxymethylcellulose or natural or synthetic polymers in the form of powders, granules or matrices, such as gum arabic, latex, polyvinylpyrrolidone, polyvinyl alcohol or polyvinyl acetate, natural phospholipids, such as cephalins or lecithins or synthetic phospholipids can be used in the, formulations. It is possible to use colourings such as inorganic, pigments, such as, for example: iron oxides, titanium oxides, Prussian blue; organic colouring stuffs, such as those of the alizarin, azo or metal phthalocyanin type; or of trace elements such as iron, manganese, boron, copper, cobalt, molybdenum or zinc salts.

The form of the pesticide composition according to the invention can, be selected in a large number of formulations, such as aerosol dispenser; suspension of, capsules; cold fogging concentrate; dustable powder; emulsifiable concentrate; aqueous/aqueous type emulsion; oil/inverse type emulsion; encapsulated granule; fine granule; suspension concentrate for seed treatment; compressed gas; gas generating product; granule; hot fogging concentrate; macrogranule; microgranule; oil-dispersible powder; oil miscible suspension concentrate; oil-miscible liquid; paste; plant rodlet; powder for dry seed treatment; seeds, coated with a pesticide; smoke maydle; smoke cartridge; smoke generator; smoke, pellet; smoke, rodlet; smoke tablet; smoke tin; soluble concentrate; soluble powder; solution for seed treatment; suspension concentrate (=flowable concentrate); ultra low volume liquid; ultra low volume suspension; vapour releasing product; water-dispersible granules or tablets; water dispersible powder for slurry treatment; water-soluble granules or tablets; water-soluble powder for seed treatment; wettable powder.

The pesticide composition according to the present invention covers not only the compositions which are ready to be applied to the crop by means of a suitable device, such as a spraying device, but also the commercial concentrated composition which have to be diluted before application to the crop.

The pesticide composition herein described is used in general for application to growing plants or to sites where crops are grown or intended to grow or, for the treatment, coating or film-coating of seeds.

According to the present invention, seeds may comprise any propagation materials, like for example seeds, fruit, tubers, grains, roots, rhizomes, parts of plants.

The pesticide composition according to the invention may also be applied to the vegetation and in particular to the leaves infested or capable of being infested with the phytopathogenic fungi or damaged by insects. Another method of applying the pesticide composition according to the invention is to add a formulation containing the active ingredients to the irrigation water.

According to another object of the present invention, there is provided a method for controlling the phytopathogenic fungi or damaging insects of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:

spraying onto the aerial parts of the said plants a liquid comprising one of the said compositions, dusting, the incorporation into the soil of granules or powders, spraying, around the said plants, and in the case of trees injection or daubing, coating or film-coating the seeds of the said plants with the aid of a plant-protection mixture comprising one of the said compositions.

The method according to the invention may either be a curing, preventing or eradicating method.

In this method, a composition used can be prepared beforehand by mixing the two or more active compounds according to the invention.

According to an alternative of such a method, it is also possible to apply simultaneously, successively or separately compounds (A), (B), (C) or (D) so as to have the conjugated (A)/(B)/(C)/(D) effects, of distinct compositions each containing one or more active ingredients (A), (B), (C) or (D).

The dose of active compound usually, applied in the method of treatment according to the invention is generally and, advantageously for foliar treatments: from 0.1 to 10,000 g/ha, preferably from 10 to 1,000 g/ha, more preferably from 50 to 300g/ha; in case of drench or drip application, the dose can even be, reduced, especially while using inert substrates like rockwool or perlite;

for seed treatment: from 2 to 200 g per 100 kilogram of seed, preferably from 3 to 150 g per 100 kilogram of seed;

for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or insect to control, a lower dose may offer adequate protection. Certain climatic conditions, resistance or other factors like the nature of the phytopathogenic fungi or damaging insect to be eliminated or the degree of infestation, for example, of the plants with these fungi, may require higher doses of combined active ingredients.

The optimum dose usually depends on, several factors, for example on the type of phytopathogenic fungus to be treated or insect to control, on the type or level of development of the infested plant, on the density of vegetation or alternatively on the method of application.

Without it being limiting, the crop, treated with the pesticide composition or combination according to the invention is, for example, grapevine, but this could be cereals vegetables, lucerne, soybean, market garden crops, turf, wood, tree or horticultural plants.

The method of treatment according to the invention may also be useful to treat propagation material such as tubers or rhizomes, but also seeds, seedlings or seedlings pricking out and plants or plants pricking out. This method of treatment may also be useful to treat roots. The method of treatment according to the invention may also be useful to treat the over-ground parts of the plant such as trunks, stems or stalks, leaves, flowers and fruit of the concerned plant.

Among the plants that may becan be protected by the method according to the invention, mention may becan be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rye, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots), *Elaeis* sp. (for instance oil palm); horticultural and forest crops; as well as genetically modified homologues of these crops.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods is which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa*, *B. juncea* (e.g. mustard) and *Brassica catinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red, cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Asparagaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (ortransgenic plants) are plants of which a heterologous gene has been stably integrated into genome. The expression "heterologous gene" essentially means a gene, which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in, the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance. Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to, the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can, sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes, which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in Brassica species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively, expressed in the tapetum cells in the stamens. Fertility, can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255,>11/943801 or 12/362,774. Plants comprising other genes that confer glyphosate tolerance, such as decarboxylase genes, are described in e.g. U.S. patent, applications Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD).

Hydroxyphenylpyruvatedioxygenases are enzymes that catalyze the reaction in which para-hydroxyphenylpyruvate (HPP) is transformed into homogentisate. Plants tolerant to HPPD-inhibitors, can be transformed with a gene, encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782 and US Patent Application No 61/288958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore of al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016 ; or
2) a crystal protein from Bacillus thuringiensis or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application No. 12/214,022 and EP 08010791.5); or
3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or
7) a hybrid, insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 5) to 7) above wherein some, particularly 1 to 10, amino acids have been replaced by another amino acid to obtain a higher insecticidal activity to a target insect species, and/or to, expand the range of target insect species affected, and/or because of changes introduced into, the encoding DNA during, cloning or transformation (while still encoding an insecticidal protein), such as the VIP3Aa protein in cotton event COT102; or
9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. Nos. 61/126083 and 61/195019), or the binary toxin made up of the VIP3 protein and the Cry2Aa or Cry2Ab or Cry2Ae proteins (U.S. patent application Ser. No. 12/214,022 and. EP 08010791.5).
10) a protein of 9) above wherein some, particularly 1 to 10, amino acids have been replaced by another amino acid, to obtain a higher insecticidal activity to a target insect species, and/or to expand the range of target insect species affected, and/or because of changes introduced into the encoding DNA during cloning or transformation (while still, encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyl-transferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as 1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO, 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed, in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as, for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549 b) Plants, such as cotton plants, containing an altered form of rsw2 or rsw3 homologous nucleic acids as described in WO 2004/053219 c) Plants, such as cotton plants, with increased expression of sucrose phosphate synthase as described in WO 01/17333 d) Plants, such as cotton plants, with increased expression of sucrose synthase as described in WO 02/45485 e) Plants, such as cotton plants, wherein the timing of the plasmodesmatal gating at the basis of the fiber cell is altered, e.g. through downregulation of fiber-selective [3-1,3-glucanase as described in WO 2005/017157, or as described in EP 08075514.3 or U.S. Patent Appl. No. 61/128,938 f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content. as described in U.S. Pat. Nos. 6,270,828, 6,169,190, or 5,965,755 c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. patent application No. 61/135,230 WO09/068313 and WO10/006732.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on, its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Further particularly transgenic plants include plants containing a transgene in an agronomically neutral or beneficial position as described in any of the patent publications listed in Table C.

TABLE A

| Trait | Reference | |
|---|---|---|
| Water use efficiency | WO 2000/073475 | |
| Nitrogen use efficiency | WO 1995/009911 | WO 2007/076115 |
| | WO 1997/030163 | WO 2005/103270 |
| | WO 2007/092704 | WO 2002/002776 |
| Improved photosynthesis | WO 2008/056915 | WO 2004/101751 |
| Nematode resistance | WO 1995/020669 | WO 2003/033651 |
| | WO 2001/051627 | WO 1999/060141 |
| | WO 2008/139334 | WO 1998/012335 |
| | WO 2008/095972 | WO 1996/030517 |
| | WO 2006/085966 | WO 1993/018170 |
| Reduced pod dehiscence | WO 2006/009649 | WO 1997/013865 |
| | WO 2004/113542 | WO 1996/030529 |
| | WO 1999/015680 | WO 1994/023043 |
| | WO 1999/000502 | |
| Aphid resistance | WO 2006/125065 | WO 2008/067043 |
| | WO 1997/046080 | WO 2004/072109 |
| Sclerotinia resistance | WO 2006/135717 | WO 2005/000007 |
| | WO 2006/055851 | WO 2002/099385 |
| | WO 2005/090578 | WO 2002/061043 |
| Botrytis resistance | WO 2006/046861 | WO 2002/085105 |
| Bremia resistance | US 20070022496 | WO 2004/049786 |
| | WO 2000/063432 | |
| Erwinia resistance | WO 2004/049786 | |
| Closterovirus resistance | WO 2007/073167 | WO 2002/022836 |
| | WO 2007/053015 | |
| Stress tolerance (including drought tolerance) | WO 2010/019838 | WO2008/002480 |
| | WO 2009/049110 | WO2005/033318 |
| Tobamovirus resistance | WO 2006/038794 | |

TABLE B

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| Petitions for Nonregulated Status Pending | | | | | |
| 10-070-01p | | Virginia Tech | Peanut | Sclerotinia blight resistant | N70, P39, and W171 |
| 09-349-01p | | Dow AgroSciences | Soybean | Herbicide Tolerant | DAS-68416-4 |
| 09-328-01p | | Bayer Crop Science | Soybean | Herbicide Tolerant | FG72 |
| 09-233-01p | | Dow | Corn | Herbicide Tolerant | DAS-40278-9 |
| 09-201-01p | | Monsanto | Soybean | | MON-87705-6 |
| 09-183-01p | | Monsanto | Soybean | | MON-87769 |
| 09-082-01p | | Monsanto | Soybean | Lepidopteran resistant | MON 87701 |
| 09-063-01p | | Stine Seed | Corn | Glyphosate tolerant | HCEM485 |
| 09-055-01p | | Monsanto | Corn | Drought Tolerant | MON 87460 |
| 09-015-01p | | BASF Plant Science, LLC | Soybean | Herbicide Tolerant | BPS-CV127-9 Soybean |
| 08-366-01p | | ArborGen | Eucalyptus | Freeze Tolerant, Fertility Altered | ARB-FTE1-08 |
| 08-340-01p | | Bayer | Cotton | Glufosinate Tolerant, Insect Resistant | T304-40XGHB119 |
| 08-338-01p | | Pioneer | Corn | Male Sterile, Fertility Restored, Visual Marker | DP-32138-1 |
| 08-315-01p | | Florigene | Rose | Altered Flower Color | IFD-52401-4 and IFD-52901-9 |
| 07-253-01p | | Syngenta | Corn | Lepidopteran resistant | MIR-162 Maize |
| 07-108-01p | | Syngenta | Cotton | Lepidopteran Resistant | COT67B |
| 06-354-01p | | Pioneer | Soybean | High Oleic Acid | DP-305423-1 |
| 05-280-01p | | Syngenta | Corn | Thermostable alpha-amylase | 3272 |
| 04-110-01p | | Monsanto & Forage Genetics | Alfalfa | Glyphosate Tolerant | J101, J163 |
| 03-104-01p | | Monsanto & Scotts | Creeping bentgrass | Glyphosate Tolerant | ASR368 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| Petitions for Nonregulated Status Granted ||||||
| 07-152-01p | | Pioneer | Corn | glyphosate & Imidazolinone tolerant | DP-098140-6 |
| 04-337-01p | | University of Florida | Papaya | Papaya Ringspot Virus Resistant | X17-2 |
| 06-332-01p | | Bayer CropScience | Cotton | Glyphosate tolerant | GHB614 |
| 06-298-01p | | Monsanto | Corn | European Corn Borer resistant | MON 89034 |
| 06-271-01p | | Pioneer | Soybean | Glyphosate & acetolactate synthase tolerant | 356043 (DP-356Ø43-5) |
| 06-234-01p | 98-329-01p | Bayer CropScience | Rice | Phosphinothricin tolerant | LLRICE601 |
| 06-178-01p | | Monsanto | Soybean | Glyphosate tolerant | MON 89788 |
| 04-362-01p | | Syngenta | Corn | Corn Rootworm Protected | MIR604 |
| 04-264-01p | | ARS | Plum | Plum Pox Virus Resistant | C5 |
| 04-229-01p | | Monsanto | Corn | High Lysine | LY038 |
| 04-125-01p | | Monsanto | Corn | Corn Rootworm Resistant | 88017 |
| 04-086-01p | | Monsanto | Cotton | Glyphosate Tolerant | MON 88913 |
| 03-353-01p | | Dow | Corn | Corn Rootworm Resistant | 59122 |
| 03-323-01p | | Monsanto | Sugar Beet | Glyphosate Tolerant | H7-1 |
| 03-181-01p | 00-136-01p | Dow | Corn | Lepidopteran Resistant & Phosphinothricin tolerant | TC-6275 |
| 03-155-01p | | Syngenta | Cotton | Lepidopteran Resistant | COT 102 |
| 03-036-01p | | Mycogen/Dow | Cotton | Lepidopteran Resistant | 281-24-236 |
| 03-036-02p | | Mycogen/Dow | Cotton | Lepidopteran Resistant | 3006-210-23 |
| 02-042-01p | | Aventis | Cotton | Phosphinothericin tolerant | LLCotton25 |
| 01-324-01p | 98-216-01p | Monsanto | Rapeseed | Glyphosate tolerant | RT200 |
| 01-206-01p | 98-278-01p | Aventis | Rapeseed | Phosphinothricin tolerant & pollination control | MS1 & RF1/RF2 |
| 01-206-02p | 97-205-01p | Aventis | Rapeseed | Phosphinothricin tolerant | Topas 19/2 |
| 01-137-01p | | Monsanto | Corn | Corn Rootworm Resistant | MON 863 |
| 01-121-01p | | Vector | Tobacco | Reduced nicotine | Vector 21-41 |
| 00-342-01p | | Monsanto | Cotton | Lepidopteran resistant | Cotton Event 15985 |
| 00-136-01p | | Mycogen c/o Dow & Pioneer | Corn | Lepidopteran resistant phosphinothricin tolerant | Line 1507 |
| 00-011-01p | 97-099-01p | Monsanto | Corn | Glyphosate tolerant | NK603 |
| 99-173-01p | 97-204-01p | Monsanto | Potato | PLRV & CPB resistant | RBMT22-82 |
| 98-349-01p | 95-228-01p | AgrEvo | Corn | Phosphinothricin tolerant and Male sterile | MS6 |
| 98-335-01p | | U. of Saskatchewan | Flax | Tolerant to soil residues of sulfonyl urea herbicide | CDC Triffid |
| 98-329-01p | | AgrEvo | Rice | Phosphinothricin tolerant | LLRICE06, LLRICE62 |
| 98-278-01p | | AgrEvo | Rapeseed | Phosphinothricin tolerant & Pollination control | MS8 & RF3 |
| 98-238-01p | | AgrEvo | Soybean | Phosphinothricin tolerant | GU262 |
| 98-216-01p | | Monsanto | Rapeseed | Glyphosate tolerant | RT73 |
| 98-173-01p | | Novartis Seeds & Monsanto | Beet | Glyphosate tolerant | GTSB77 |
| 98-014-01p | 96-068-01p | AgrEvo | Soybean | Phosphinothricin tolerant | A5547-127 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 97-342-01p | | Pioneer | Corn | Male sterile & Phosphinothricin tolerant | 676, 678, 680 |
| 97-339-01p | | Monsanto | Potato | CPB & PVY resistant | RBMT15-101, SEMT15-02, SEMT15-15 |
| 97-336-01p | | AgrEvo | Beet | Phosphinothricin tolerant | T-120-7 |
| 97-287-01p | | Monsanto | Tomato | Lepidopteran resistant | 5345 |
| 97-265-01p | | AgrEvo | Corn | Phosphinothricin tolerant & Lep. resistant | CBH-351 |
| 97-205-01p | | AgrEvo | Rapeseed | Phosphinothricin tolerant | T45 |
| 97-204-01p | | Monsanto | Potato | CPB & PLRV resistant | RBMT21-129 & RBMT21-350 |
| 97-148-01p | | Bejo | *Cichorium intybus* | Male sterile | RM3-3, RM3-4, RM3-6 |
| 97-099-01p | | Monsanto | Corn | Glyphosate tolerant | GA21 |
| 97-013-01p | | Calgene | Cotton | Bromoxynil tolerant & Lepidopteran resistant | Events 31807 & 31808 |
| 97-008-01p | | Du Pont | Soybean | Oil profile altered | G94-1, G94-19, G-168 |
| 96-317-01p | | Monsanto | Corn | Glyphosate tolerant & ECB resistant | MON802 |
| 96-291-01p | | DeKalb | Corn | European Corn Borer resistant | DBT418 |
| 96-248-01p | 92-196-01p | Calgene | Tomato | Fruit ripening altered | 1 additional FLAVRSAVR line |
| 96-068-01p | | AgrEvo | Soybean | Phosphinothricin tolerant | W62, W98, A2704-12, A2704-21, A5547-35 |
| 96-051-01p | | Cornell U | Papaya | PRSV resistant | 55-1, 63-1 |
| 96-017-01p | 95-093-01p | Monsanto | Corn | European Corn Borer resistant | MON809 & MON810 |
| 95-352-01p | | Asgrow | Squash | CMV, ZYMV, WMV2 resistant | CZW-3 |
| 95-338-01p | | Monsanto | Potato | CPB resistant | SBT02-5 & -7, ATBT04-6 & -27, -30, -31, -36 |
| 95-324-01p | | Agritope | Tomato | Fruit ripening altered | 35 1 N |
| 95-256-01p | | Du Pont | Cotton | Sulfonylurea tolerant | 19-51a |
| 95-228-01p | | Plant Genetic Systems | Corn | Male sterile | MS3 |
| 95-195-01p | | Northrup King | Corn | European Corn Borer resistant | Bt11 |
| 95-179-01p | 92-196-01p | Calgene | Tomato | Fruit ripening altered | 2 additional FLAVRSAVR lines |
| 95-145-01p | | DeKalb | Corn | Phosphinothricin tolerant | B16 |
| 95-093-01p | | Monsanto | Corn | Lepidopteran resistant | MON 80100 |
| 95-053-01p | | Monsanto | Tomato | Fruit ripening altered | 8338 |
| 95-045-01p | | Monsanto | Cotton | Glyphosate tolerant | 1445, 1698 |
| 95-030-01p | 92-196-01p | Calgene | Tomato | Fruit ripening altered | 20 additional FLAVRSAVR lines |
| 94-357-01p | | AgrEvo | Corn | Phosphinothricin tolerant | T14, T25 |
| 94-319-01p | | Ciba Seeds | Corn | Lepidopteran resistant | Event 176 |
| 94-308-01p | | Monsanto | Cotton | Lepidopteran resistant | 531, 757, 1076 |
| 94-290-01p | | Zeneca & Petoseed | Tomato | Fruit polygalacturonase level decreased | B, Da, F |
| 94-257-01p | | Monsanto | Potato | Coleopteran resistant | BT6, BT10, BT12, BT16, BT17, BT18, BT23 |
| 94-230-01p | 92-196-01p | Calgene | Tomato | Fruit ripening altered | 9 additional FLAVRSAVR lines |
| 94-228-01p | | DNA Plant Tech | Tomato | Fruit ripening altered | 1345-4 |
| 94-227-01p | 92-196-01p | Calgene | Tomato | Fruit ripening altered | Line N73 1436-111 |
| 94-090-01p | | Calgene | Rapeseed | Oil profile altered | pCGN3828-212/86- 18 & 23 |
| 93-258-01p | | Monsanto | Soybean | Glyphosate tolerant | 40-3-2 |
| 93-196-01p | | Calgene | Cotton | Bromoxynil tolerant | BXN |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 92-204-01p | | Upjohn | Squash | WMV2 & ZYMV resistant | ZW-20 |
| 92-196-01p | | Calgene | Tomato | Fruit ripening altered | FLAVR SAVR |

NOTE:
To obtain the most up-to-date list of Crops No Longer Regulated, please look at the Current Status of Petitions. This list is automatically updated and reflects all petitions received to date by APHIS, including petitions pending, withdrawn, or approved.
Abbreviations:
CMV—cucumber mosaic virus; CPB—colorado potato beetle; PLRV—potato leafroll virus; PRSV—papaya ringspot virus; PVY—potato virus Y; WMV2—watermelon mosaic virus 2 ZYMV—zucchini yellow mosaic virus
*** Extension of Petition Number: Under 7CFR 340.6(e) a person may request that APHIS extend a determination of non-regulated status to other organisms based on their similarity of the previously deregulated article. This column lists the previously granted petition of that degregulated article.
**** Preliminary EA: The Environmental Assessment initially available for Public comment prior to finalization.

TABLE C

| Plant species | Event | Trait | Patent reference |
|---|---|---|---|
| Corn | PV-ZMGT32 (NK603) | Glyphosate tolerance | US 2007-056056 |
| Corn | MIR604 | Insect resistance (Cry3a055) | EP 1 737 290 |
| Corn | LY038 | High lysine content | U.S. Pat. No. 7,157,281 |
| Corn | 3272 | Self processing corn (alpha-amylase) | US 2006-230473 |
| Corn | PV-ZMIR13 (MON863) | Insect resistance (Cry3Bb) | US 2006-095986 |
| Corn | DAS-59122-7 | Insect resistance (Cry34Ab1/Cry35Ab1) | US 2006-070139 |
| Corn | TC1507 | Insect resistance (Cry1F) | U.S. Pat. No. 7,435,807 |
| Corn | MON810 | Insect resistance (Cry1Ab) | US 2004-180373 |
| Corn | VIP1034 | Insect resistance | WO 03/052073 |
| Corn | B16 | Glufosinate resistance | US 2003-126634 |
| Corn | GA21 | Glyphosate resistance | U.S. Pat. No. 6,040,497 |
| Corn | GG25 | Glyphosate resistance | U.S. Pat. No. 6,040,497 |
| Corn | GJ11 | Glyphosate resistance | U.S. Pat. No. 6,040,497 |
| Corn | FI117 | Glyphosate resistance | U.S. Pat. No. 6,040,497 |
| Corn | GAT-ZM1 | Glufosinate tolerance | WO 01/51654 |
| Corn | MON87460 | Drought tolerance | WO 2009/111263 |
| Corn | DP-098140-6 | Glyphosate tolerance/ALS inhibitor tolerance | WO 2008/112019 |
| Wheat | Event 1 | Fusarium resistance (trichothecene 3-O-acetyltransferase) | CA 2561992 |
| Sugar beet | T227-1 | Glyphosate tolerance | US 2004-117870 |
| Sugar beet | H7-1 | Glyphosate tolerance | WO 2004-074492 |
| Soybean | MON89788 | Glyphosate tolerance | US 2006-282915 |
| Soybean | A2704-12 | Glufosinate tolerance | WO 2006/108674 |
| Soybean | A5547-35 | Glufosinate tolerance | WO 2006/108675 |
| Soybean | DP-305423-1 | High oleic acid/ALS inhibitor tolerance | WO 2008/054747 |
| Rice | GAT-OS2 | Glufosinate tolerance | WO 01/83818 |
| Rice | GAT-OS3 | Glufosinate tolerance | US 2008-289060 |
| Rice | PE-7 | Insect resistance (Cry1Ac) | WO 2008/114282 |
| Oilseed rape | MS-B2 | Male sterility | WO 01/31042 |
| Oilseed rape | MS-BN1/RF-BN1 | Male sterility/restoration | WO 01/41558 |
| Oilseed rape | RT73 | Glyphosate resistance | WO 02/36831 |
| Cotton | CE43-67B | Insect resistance (Cry1Ab) | WO 2006/128573 |
| Cotton | CE46-02A | Insect resistance (Cry1Ab) | WO 2006/128572 |
| Cotton | CE44-69D | Insect resistance (Cry1Ab) | WO 2006/128571 |
| Cotton | 1143-14A | Insect resistance (Cry1Ab) | WO 2006/128569 |
| Cotton | 1143-51B | Insect resistance (Cry1Ab) | WO 2006/128570 |
| Cotton | T342-142 | Insect resistance (Cry1Ab) | WO 2006/128568 |
| Cotton | event3006-210-23 | Insect resistance (Cry1Ac) | WO 2005/103266 |
| Cotton | PV-GHGT07 (1445) | Glyphosate tolerance | US 2004-148666 |
| Cotton | MON88913 | Glyphosate tolerance | WO 2004/072235 |
| Cotton | EE-GH3 | Glyphosate tolerance | WO 2007/017186 |
| Cotton | T304-40 | Insect-resistance (Cry1Ab) | WO2008/122406 |
| Cotton | Cot202 | Insect resistance (VIP3) | US 2007-067868 |
| Cotton | LLcotton25 | Glufosinate resistance | WO 2007/017186 |
| Cotton | EE-GH5 | Insect resistance (Cry1Ab) | WO 2008/122406 |
| Cotton | event 281-24-236 | Insect resistance (Cry1F) | WO 2005/103266 |

TABLE C-continued

| Plant species | Event | Trait | Patent reference |
|---|---|---|---|
| Cotton | Cot102 | Insect resistance (Vip3A) | US 2006-130175 |
| Cotton | MON 15985 | Insect resistance (Cry1A/Cry2Ab) | US 2004-250317 |
| Bent Grass | Asr-368 | Glyphosate tolerance | US 2006-162007 |
| Brinjal | EE-1 | Insect resistance (Cry1Ac) | WO 2007/091277 |

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the, invention; this includes for example direct application, spraying, dipping, injection or any other suitable means.

Among the diseases of plants or crops that can be controlled by the method according to the invention, mention can be made of Powdery Mildew Diseases such as Blumeria diseases caused for example by Blumeria graminis;
Podosphaera diseases caused for example by Podosphaera, leucotricha;
Sphaerotheca diseases caused for example by Sphaerotheca fuliginea;
Uncinula diseases caused for example by Uncinula necator;
  Rust Diseases such as
Gymnosporangium diseases caused for example by Gymnosporangium sabinae;
Hemileia diseases caused for example by Hemileia vastatrix;
Phakopsora diseases caused for example by Phakopsora pachyrhizi and Phakopsora meibomiae;
Puccinia diseases caused for example by Puccinia recondita, Puccinia graminis or Puccinia striiformis;
Uromyces diseases caused for example by Uromyces appendiculatus;
  Oomycete Diseases such as
Albugo diseases caused for example by Albugo candida;
Bremia diseases caused for example by Bremia lactucae;
Peronospora diseases caused for example by Peronospora pisi and Peronospora brassicae;
Phytophthora diseases caused for example by Phytophthora infestans;
Plasmopara diseases caused for example by Plasmopara viticola;
Pseudoperonospora diseases caused for example by Pseudoperonospora humuli and Pseudo-peronospora cubensis;
Pythium diseases caused for example by Pythium ultimum;
  Leaf spot, Leaf blotch and Leaf Blight Diseases such as
Alternaria diseases caused for example by Alternaria solani;
Cercospora diseases caused for example by Cercospora beticola;
Cladiosporium diseases caused for example by Cladiosporium cucumerinum;
Cochliobolus diseases caused for example by Cochliobolus sativus (Conidiaform: Drechslera, Syn: Helminthosporium) or Cochliobolus miyabeanus;
Colletotrichum diseases caused for example by Colletotrichum lindemuthianum;
Cycloconium diseases caused for example by Cycloconium oleaginum;
Diaporthe diseases caused for example by Diaporthe citri;
Elsinoe diseases caused for example by Elsinoe fawcettii;
Gloeosporium diseases caused for example by Gloeosporium laeticolor;
Glomerella diseases caused for example by Glomerella cingulata;
Guignardia diseases caused for example by Guignardia bidwellii;
Leptosphaeria diseases caused for example by Leptosphaeria maculans and Leptosphaeria nodorum;
Magnaporthe diseases caused for example by Magnaporthe grisea;
Mycosphaerella diseases caused for example by Mycosphaerella graminicola, Mycosphaerella arachidicola and Mycosphaerella fijiensis;
Phaeosphaeria diseases caused for example by Phaeosphaeria nodorum;
Pyrenophora diseases caused for example by Pyrenophora teres or Pyrenophora tritici repentis;
Ramularia—diseases caused for example by Ramularia collo-cygni or Ramularia areola;
Rhynchosporium diseases caused for example by Rhynchosporium secalis;
Septoria diseases caused for example by Septoria apii and Septoria lycopersici;
Typhula diseases caused for example by Thyphula incarnata;
Venturia diseases caused for example by Venturia inaequalis;
  Root—, Sheath and Stem Diseases such as
Corticium diseases caused for example by Corticium graminearum;
Fusarium diseases caused for example by Fusarium oxysporum;
Gaeumannomyces diseases caused for example by Gaeumannomyces graminis;
Rhizoctonia diseases caused for example by Rhizoctonia solani;
Sarocladium diseases caused for example by Sarocladium oryzae;
Sclerotium diseases caused for example by Sclerotium oryzae;
Tapesia diseases caused for example by Tapesia acuformis;
Thielaviopsis diseases caused for example by Thielaviopsis basicola;
  Ear and Panicle Diseases including Maize cob such as
Alternaria diseases caused for example by Alternaria spp.;
Aspergillus diseases caused for example by Aspergillus flavus;
Cladosporium diseases caused for example by Cladosporium cladosporioides;
Claviceps diseases caused for example by Claviceps purpurea;
Fusarium diseases caused for example by Fusarium culmorum;
Gibberella diseases caused for example by Gibberella zeae;
Monographella diseases caused for example by Monographella nivalis;
  Smut- and Bunt Diseases such as

*Sphacelotheca* diseases caused for example by *Sphacelotheca reiliana*;
*Tilletia* diseases caused for example by *Tilletia caries*;
*Urocystis* diseases caused for example by *Urocystis occulta*;
*Ustilago* diseases caused for example by *Ustilago nuda*;
Fruit Rot and Mould Diseases such as
*Aspergillus* diseases caused for example by *Aspergillus flavus*;
*Botrytis* diseases caused for example by *Botrytis cinerea*;
*Penicillium* diseases caused for example by *Penicillium expansum* and *Penicillium purpurogenum*;
*Rhizopus* diseases caused by example by *Rhizopus stolonifer*
*Sclerotinia* diseases caused for example by *Sclerotinia sclerotiorum*;
*Verticillium* diseases caused for example by *Verticillium alboatrum*;
Seed- and Soilborne Decay, Mould, Wilt, Rot and Damping-off diseases
*Alternaria* diseases caused for example by *Alternaria brassicicola*;
*Aphanomyces* diseases caused for example by *Aphanomyces euteiches*;
*Ascochyta* diseases caused for example by *Ascochyta lentis*;
*Aspergillus* diseases caused for example by *Aspergillus flavus*;
*Cladosporium* diseases caused for example by *Cladosporium herbarum*;
*Cochliobolus* diseases caused for example by *Cochliobolus sativus*;
(Conidiaform: Drechslera, Bipolaris Syn: *Helminthosporium*);
*Colletotrichum* diseases caused for example by *Colletotrichum coccodes*;
*Fusarium* diseases caused for example by *Fusarium culmorum*;
*Gibberella* diseases caused for example by *Gibberella zeae*;
*Macrophomina* diseases caused for example by *Macrophomina phaseolina*;
*Microdochium* diseases caused for example by *Microdochium nivale*;
*Monographella* diseases caused for example by *Monographella nivalis*;
*Penicillium* diseases caused for example by *Penicillium expansum*;
*Phoma* diseases caused for example by *Phoma lingann*;
*Phomopsis* diseases caused for example by *Phomopsis sojae*;
*Phytophthora* diseases caused for example by *Phytophthora cactorum*;
*Pyrenophora* diseases caused for example by *Pyrenophora graminea*;
*Pyricularia* diseases caused for example by *Pyricularia oryzae*;
*Pythium* diseases caused for example by *Pythium ultimum*;
*Rhizoctonia* diseases caused for example by *Rhizoctonia solani*;
*Rhizopus* diseases caused for example by *Rhizopus oryzae*;
*Sclerotium* diseases caused for example by *Sclerotium rolfsii*;
*Septoria* diseases caused for example by *Septoria nodorum*;
*Typhula* diseases caused for example by *Typhula incarnata*;
*Verticillium* diseases caused for example by *Verticillium dahliae*;
Canker, Broom and Dieback Diseases such as
*Nectria* diseases caused for example by *Nectria galligena*;
Blight Diseases such as
*Monilinia* diseases caused for example by *Monilinia laxa*;

Leaf Blister or Leaf Curl Diseases including deformation of blooms and fruits such as
*Exobasidium* diseases caused for example by *Exobasidium vexans*.
*Taphrina* diseases caused for example by *Taphrina deformans*;
Decline Diseases of Wooden Plants such as
*Esca* disease caused for example by *Phaeornoniella clannydospora*, *Phaeoacremonium aleophilum* and *Fomitiporia mediterranea*;
*Ganoderma* diseases caused for example by *Ganoderrna boninense*;
*Rigidoporus* diseases caused for example by *Rigidoporus lignosus*
Diseases of Flowers and Seeds such as
*Botrytis* diseases caused for example by *Botrytis cinerea*;
Diseases of Tubers such as
*Rhizoctonia* diseases caused for example by *Rhizoctonia solani*;
*Helminthosporium* diseases caused for example by *Helminthosporium solani*;
Club root diseases such as
*Plasmodiophora* diseases, cause for example by *Plamodiophora brassicae*.
Diseases caused by Bacterial Organisms such as
*Xanthomonas* species for example *Xanthomonas campestris* pv. *oryzae*;
*Pseudomonas* species for example *Pseudomonas syringae* pv. *lachrymans*;
*Erwinia* species for example *Erwinia amylovora*.

The damaging insects of crops which can be controlled at any development stage by using the pesticide composition according to the invention, include:

pests from the order of Isopoda for example *Oniscus asellus, Armadillidium vulgare, Porcellio scaber*;
pests from the order of Diplopoda for example *Blaniulus guttulatus*;
pests from the order of Chilopoda for example *Geophilus carpophagus, Scutigera* spp.;
pests from the order of Symphyla for example *Scutigerella immaculata*;
pests from the order of Thysanura for example *Lepisma saccharina*;
pests from the order of Collembola for example *Onychiurus armatus*;
pests from the order of Orthoptera for example *Acheta domesticus, Gryllotalpa* spp., *Locusta migratoria migratorioides, Melanoplus* spp., *Schistocerca gregaria*;
pests from the order of Blattaria for example *Blatta orientalis, Periplaneta americana, Leucophaea maderae, Blattella germanica*;
pests from the order of Dermaptera for example *Forficula auricularia*;
pests from the order of Isoptera for example *Reticulitermes* spp.;
pests from the order of Phthiraptera for example *Pediculus humanus corporis, Haematopinus* spp., *Linognathus* spp., *Trichodectes* spp., *Damalinia* spp.;
pests from the order of Thysanoptera for example *Hercinothrips femoralis, Thrips tabaci, Thrips palmi, Frankliniella accidentalis*;
pests from the order of Heteroptera for example *Eurygaster* spp., *Dysdercus intermedius, Piesma quadrata, Cimex lectularius, Rhodnius prolixus, Triatoma* spp;
pests from the order of Hornoptera for example *Aleurodes brassicae, Bemisia tabaci, Trialeurodes vaporariorum*,

*Aphis gossypii, Brevicoryne brassicae, Cryptornyzus ribis, Aphis fabae, Aphis porni, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp;

pests from the order of Lepidoptera for example *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae;* pests from the order of Coleoptera for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp. *oryzaephilus surinamensis, Anthonomus* spp., *Sitophilus* spp., *Otiorrhynchus sulcatus, Cosmopolites sordidus, Ceuthorrhynchus assimilis, Hypera, postica, Dermestes* spp., *Trogoderma* spp., *Anthrenus* spp., *Attagenus*, spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus;* pests from the order of Hymenoptera for example *Diprion* spp., *Hoplocampa* spp., *Lasius* spp., *Monomorium pharaonis, Vespa* spp;

pests from the order of Diptera for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.;

pests from the order of Siphonaptera for example *Xenopsylla cheopis, Ceratophyllus* spp.;

pests from the class of Arachnida for example *Scorpio maurus, Latrodectus mactans, Acarus siro, Argas* spp. *ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp;

the plant-parasitic nematodes such as *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

As a further aspect, the present invention provides products comprising compounds (A) and (B); (A), (B) and (C); (A), (B) and (D); or (A), (B), (C) and (D) as herein defined, as a combined preparation for simultaneous, separate or sequential use in controlling the phytopathogenic fungi or damaging insects of plants, crops or seeds at a site.

The pesticide composition according to the invention can be prepared immediately before use by using a kit-of-parts for controlling, curatively or preventively, the phytopathogenic fungi of crops, such a kit-of-parts may comprise at least one or several compounds (A), (B), (C) and/or (D) intended to be combined or used simultaneously, separately or sequentially in controlling the phytopathogenic fungi of crops at a site.

It is therefore a pack wherein the user finds all the ingredients for preparing the, fungicide formulation which they wish, to apply to the crops. These ingredients, which comprise in particular the active agents (A), (B), (C) and/or (D) and which are packaged, separately, are provided in the form of a powder or in the form of a liquid which is concentrated to a greater or lesser degree. The user simply has to mix in the prescribed doses and to add the quantities of liquid, for example of water, necessary to obtain a formulation which is ready to use and which can be applied to the crops.

The advanced fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually. The expected activity for a given combination of two active compounds can be calculated as follows (cf. Colby, S. R., "Calculating Synergistic and Antagonistic Responses of Herbicide Combinations", *Weeds* 1967, 15, 20-22):

If

X is the efficacy when active, compound A is applied at an, application rate of m ppm (or g/ha), Y is the efficacy when active compound B is applied at an application rate of n ppm (or g/ha), E is the efficacy when the active compounds A and B are applied at application rates of m and n ppm (or g/ha), respectively, and then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating, a synergistic effect is the method of Tammes (cf. "Isoboles, a graphic representation of synergism in, pesticides" in *Neth. J. Plant Path.,* 1964, 70, 73-80).

The invention is illustrated by the following example. However the invention is not limited to the examples.

Example

Phytophthora Test (Tomatoes)/Preventive
Solvent: 24,5 parts by weight of acetone
24,5 parts by weight of dimethylacetamide
Emulsifier: part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on the plants are inoculated with an aqueous spore suspension of Phytophthora infestans. The plants are then placed in an incubation cabinet at approximately 20° C. and a relative atmospheric humidity of 100%.

The test is evaluated 3 days after the inoculation. 0% means an efficacy which corresponds to that of the untreated control, while an efficacy of 100% means that no disease is observed.

The table below clearly shows that the observed activity of the active compound combination according to the invention is greater than the calculated activity, i.e. a synergistic effect is present.

Example

Venturia Test (Apples)/Preventive
Solvent: 24,5 parts by weight of acetone
24,5 parts by weight of dimethylacetamide
Emulsifier: part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

TABLE

*Phytophthora* test (tomatoes)/protective

|  | Active compounds | Application rate of active compound in ppm a.i. | Efficacy in % found* | calc.** |
|---|---|---|---|---|
| (A2) | tert-butyl {6-[({[(Z)-(1-methyl-1H-tetrazol-5-yl)(phenyl)methylene]-amino}oxy)methyl]pyridin-2-yl}-carbamate | 1 | 46 | |
| (B2) | 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]-ethanone | 0.01 | 30 | |
| (A2) + (B2) | 100:1 | 1 + 0.01 | 73 | 62 |

*found = activity found
**calc. = activity calculated using Colby's formula

The table below clearly shows that the observed activity of the active compound combination according to the invention is greater than the calculated activity, i.e. a synergistic effect is present.

TABLE

*Venturia* test (apples)/preventive

|  | Active compounds | Application rate of active compound in ppm a.i. | Efficacy in % found* | calc.** |
|---|---|---|---|---|
| (A2) | tert-butyl {6-[({[(Z)-(1-methyl-1H-tetrazol-5-yl)(phenyl)methylene]-amino}oxy)methyl]pyridin-2-yl}-carbamate | 100 | 22 | |
| (B2) | 1-(4-{4-[5-(2,6-difluorophenyl)-4,5-dihydro-1,2-oxazol-3-yl]-1,3-thiazol-2-yl}piperidin-1-yl)-2-[5-methyl-3- | 100 | 0 | |

| Venturia test (apples)/preventive | | | |
|---|---|---|---|
| | Application rate of active compound in | Efficacy in % | |
| Active compounds | ppm a.i. | found* | calc.** |
| (trifluoromethyl)-1H-pyrazol-1-yl]-ethanone | | | |
| (A2) + (B2)  1:1 | 100 + 100 | 56 | 22 |

*found = activity found
**calc. = activity calculated using Colby's formula

The invention claimed is:

1. A composition comprising:

A) a tetrazolyloxime derivative of formula (I)

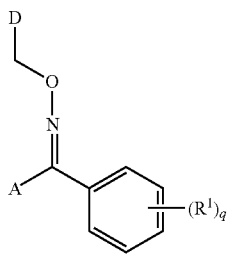

(I)

wherein $R^1$ independently represents a hydrogen atom;

q represents 0, 1, 2, 3, 4 or 5;

A represents a tetrazoyl group of formula ($A^1$):

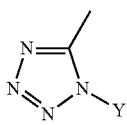

($A^1$)

wherein Y represents an $C_1$-$C_6$-alkyl group; and

D represents a pyridyl group of formula ($D^1$);

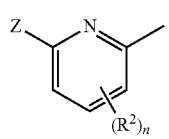

($D^1$)

wherein $R^2$ represents a hydrogen atom;

wherein n represents 0, 1, 2 or 3;

wherein Z represents $Q^1$CONH—, wherein $Q^1$ represents a non-substituted $C_1$-$C_8$-alkyl, or non-substituted $C_1$-$C_8$-alkoxy;

as well as salts, N-oxides, metallic complexes and metalloidic complexes thereof or (E) and (Z) isomers and mixtures thereof and B) a thiazolylpiperidine derivative of formula (II)

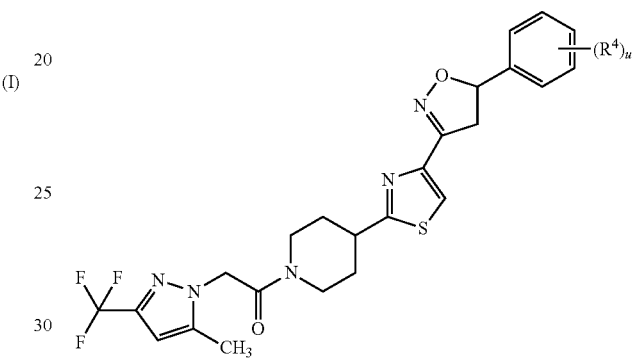

(II)

wherein $R^4$ independently represents a hydrogen atom, a halogen atom, a $C_1$-$C_6$-alkyl, a $C_1$-$C_6$-alkoxy, a $C_1$-$C_6$-haloalkyl comprising between one and 5 halogen atoms, cyano;

u represents 1, 2, 3, 4 or 5;

as well as salts, N-oxides, metallic complexes and metalloidic complexes thereof or optically active isomers and mixtures thereof;

in an A/B weight ratio ranging from 1,000/1 to 1/1,000.

2. A composition according to claim 1 wherein Y represents a methyl group.

3. A composition according to claim 1 wherein $R^4$ independently represents a hydrogen atom or a halogen atom.

4. A composition according to claim 1 wherein $R^4$ represents a hydrogen atom or a fluorine.

5. A composition according to claim 1 wherein the tetrazolyloxime derivative of formula (I) is tert-butyl{6-[{]([(Z)-(1-methyl-1H-tetrazol-5-yl) (phenyl)methylene]amino}oxy) methyl pyridin-2-yl}carbamate.

6. A composition according to claim 1 wherein the thiazolylpiperidine derivative of formula (II) is 2-[5-methyl-3-(trifluoromethyl)-1H-pyrazol-1-yl]-1-{4-[4-(5-phenyl-4,5-dihydro-1,2-oxazol-3 -yl)-1,3-thiazol-2]piperidin-1-yl}ethanone or 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone.

7. A composition according to claim 1 further comprising
C) a third fungicide compound,
in an A/B/C weight ratio ranging from 1,000/1,000/1 to 1/1,000/1,000.

8. A composition according to claim 1 further comprising
D) an insecticide compound,
in an A/B/D weight ratio ranging from 1,000/1,000/1 to 1/1,000/1,000.

9. A composition according to claim 1 further comprising
C) a third further fungicide compound and
D) an insecticide compound, in an A/B/C/D weight ratio ranging from 1,000/1,000/1,000/1 to 1/1,000/1,000/1,000.

10. A method for controlling the phytopathogenic fungi or damaging insects of plants, crops or seeds comprising the step of applying an agronomically effective and substantially non-phytotoxic quantity of a pesticide composition according to claim 1 as seed treatment, foliar application, stem application, drench or drip application or chemigation to the seed, the plant or to the fruit of the plant or to soil or to inert substrate, Pumice, Pyroclastic materials or stuff, synthetic organic substrates organic substrates or to a liquid substrate wherein the plant is growing or wherein it is desired to grow.

11. A composition according to claim 1, wherein Y is a methyl group, $Q^1$ is a non-substituted $C_1$-$C_6$-alkoxy and $R^4$ is a hydrogen or halogen atom.

12. A composition according to claim 1, wherein Y is a methyl group, $Q^1$ is a non-substituted $C_1$-$C_6$-alkoxy and $R^4$ is a hydrogen or halogen atom and u is 2.

13. A composition according to claim 1, wherein the tetrazolyoxime derivative of formula (I) is tert-butyl tert-butyl{6-[({[(Z)-(1-methyl-1H-tetrazol-5-yl) (phenyl)methylene]amino}oxy)methyl]pyridin-2-yl}carbamate and the thiazolylpiperidine derivative of formula (II) is 1-(4-{4-[5-(2,6-difluorophenyl) -4,5-dihydro-1,2-oxazol-3-yl]-1,3-thiazol-2-yl}piperidin-1-yl)-2-[5-methyl-3-(trifluoromethyl)-1H-pyrazol-1-yl]ethanone.

\* \* \* \* \*